United States Patent [19]

Grimberg

[11] Patent Number: 5,587,177
[45] Date of Patent: Dec. 24, 1996

[54] MEDICAMENT HAVING A PEDIATRIC PRESENTATION FOR FACILITATING THE INGESTION THEREOF BY A CHILD

[76] Inventor: Georges S. Grimberg, 123 rue de l'Université', 75007 Paris, France

[21] Appl. No.: 376,837

[22] Filed: Jan. 23, 1995

[30] Foreign Application Priority Data

Jan. 21, 1994 [FR] France ................................. 94 00639

[51] Int. Cl.$^6$ ........................................................ A61K 9/48
[52] U.S. Cl. ......................... 424/454; 424/451; 424/453; 424/439
[58] Field of Search ................................. 424/451, 454, 424/453, 439

[56] References Cited

U.S. PATENT DOCUMENTS

| | | | |
|---|---|---|---|
| 4,076,848 | 2/1978 | de Limur | 426/89 |
| 5,484,598 | 1/1996 | Schurig et al. | 424/401 |

FOREIGN PATENT DOCUMENTS

| | | |
|---|---|---|
| 0058584 | 8/1982 | European Pat. Off. . |
| 8806558 | 9/1988 | WIPO . |

*Primary Examiner*—James M. Spear
*Attorney, Agent, or Firm*—Robert W. Becker & Associates

[57] ABSTRACT

A capsule contains a unit dose of a medicament and is formed by a small container with a cup-shaped hollow bottom. The bottom has a top portion connected by a flexible strip to a cover of a suitable matching shape. A catch is provided for maintaining the cover on the cup-shaped bottom. The catch is easily operated for opening the capsule containing the unit dose. The capsule cannot be closed again once open.

4 Claims, 1 Drawing Sheet

MEDICAMENT HAVING A PEDIATRIC PRESENTATION FOR FACILITATING THE INGESTION THEREOF BY A CHILD

FIELD OF THE INVENTION

This invention relates to a medicament having a pediatric presentation for facilitating the ingestion thereof by a child.

BACKGROUND OF THE INVENTION

Giving a medicament to a young child requires an acceptance of the medicament by the child. It is thus necessary that the medicament is sweetened and flavored.

The liquid form is the easiest form to prepare and in which to give a medicament to the child. However, the liquid form has two drawbacks:

preservatives in amounts that are relatively important with respect to the weight of the child must be incorporated in the liquid; and the liquid must be taken with a spoon; the dosage accuracy is thus never perfect and, furthermore, the medicament may happen to be taken not during a meal, but on an empty stomach.

If the product is, for example, a salt of magnesium, it must be taken with food. Actually, for some children, magnesium salt products will cause diarrhoea and stomach pains when taken without food.

An object of the present invention is to provide a powder that can be mixed with food in a perfectly dosed amount, and therefore a powder in unit dose and of a small volume. The above phrase "of a small volume" must be emphasized since there exists a medicament in the form in small bags, but they must have a relatively large volume, since the medicament comprises some excipients which, generally, are not suitable for a young child.

Moreover, there exists unit doses in a dry form which are to be swallowed, for example tablets or capsules. In some cases, these forms are dangerous to swallow and can cause stomach problems, or they are eliminated without having been absorbed by the body.

Capsules are known by U.S. Pat. No. 4,076,848 to De Limur which contain a pulverized dehydrated fruit and vegetable product provided to flavor various kinds of food dishes. These capsules are therefore designed to be easily opened and then re-closed, in order to choose the desired amount of product.

The present invention provides a capsule of a fully different type. Actually, this capsule is easily openable in order to enable the mother of the child to pour the whole content of this capsule, for example, a powder of a magnesium salt to which is added a sweetener or a flavoring agent, into a food that is easily accepted by a young child, such as yogurt, custard or a similar product.

It is thus clear that the purpose of the present invention is totally different from that of the above U.S. Pat. No. 4,076,848 to De Limur. The present invention relates actually to a powdered medicament to be taken in the form of a unit dose. Thus, each capsule contains a certain amount of a perfectly dosed powder and must be easily openable. This capsule is not designed to be re-closeable, since the capsule must be completely emptied once open.

SUMMARY OF THE INVENTION

According to the present invention, the combination of a medicament with a capsule having a pediatric presentation facilitating ingestion of the medicament by a child is primarily characterized by: the capsule containing a unit dose of the medicament and formed by a small container comprising a cup-shaped bottom with a top portion; a cover having a shape matching the shape of the cup-shaped bottom; a flexible strip for connecting the top portion to the cover; wherein the capsule further comprises a catch for maintaining the cover on the cup-shaped bottom, the catch being easily operated for opening the capsule, and wherein the capsule once open cannot be closed again.

Preferably, the medicament is an anhydrous powder mixable with food so as to be easily ingested by a child.

Advantageously, the medicament is comprised of:

| | |
|---|---|
| magnesium sulphate × 3H$_2$O | 355 mg |
| saccharomyces yeast | 50 mg |
| sodium saccharinate | 5 mg |
| sodium cyclamate | 10 mg |
| citric acid | 10 mg |
| orange flavoring agent | 10 mg |
| Aerosil | 1 mg |

Expediently, the unit dose comprises a therapeutically active ingredient as the main ingredient.

According to the invention, the capsule contains a medicamentous dose and is formed by a small container with a cup-shaped hollow bottom, the container having a top portion connected by a flexible strip to a cover of a suitable corresponding shape, a valve (flap valve) being provided for maintaining the cover on the cup-shaped container, the valve being easily operated for opening the capsule containing said medicamentous dose, said open capsule being then non-closable.

According to another feature of the invention, the medicamentous dose is in the form of an anhydrous powder, preferably easily mixable with a liquid, semi-liquid or pasty food so as to be easily ingested by a young child.

According to still another feature of the invention, the medicamentous dose contains powder capsule:

| | |
|---|---|
| Magnesium sulphate, 3H$_2$O | 355 mg |
| Saccharomyces yeast | 50 mg |
| Sodium saccharinate | 5 mg |
| Sodium cyclamate | 10 mg |
| Citric acid | 10 mg |
| Orange flavoring agent | 10 mg |
| Aerosil | 1 mg |

Various other features of the invention will moreover be revealed from the following detailed disclosure.

BRIEF DESCRIPTION OF THE DRAWING

The only drawing

DESCRIPTION OF PREFERRED EMBODIMENTS

Figure 1:
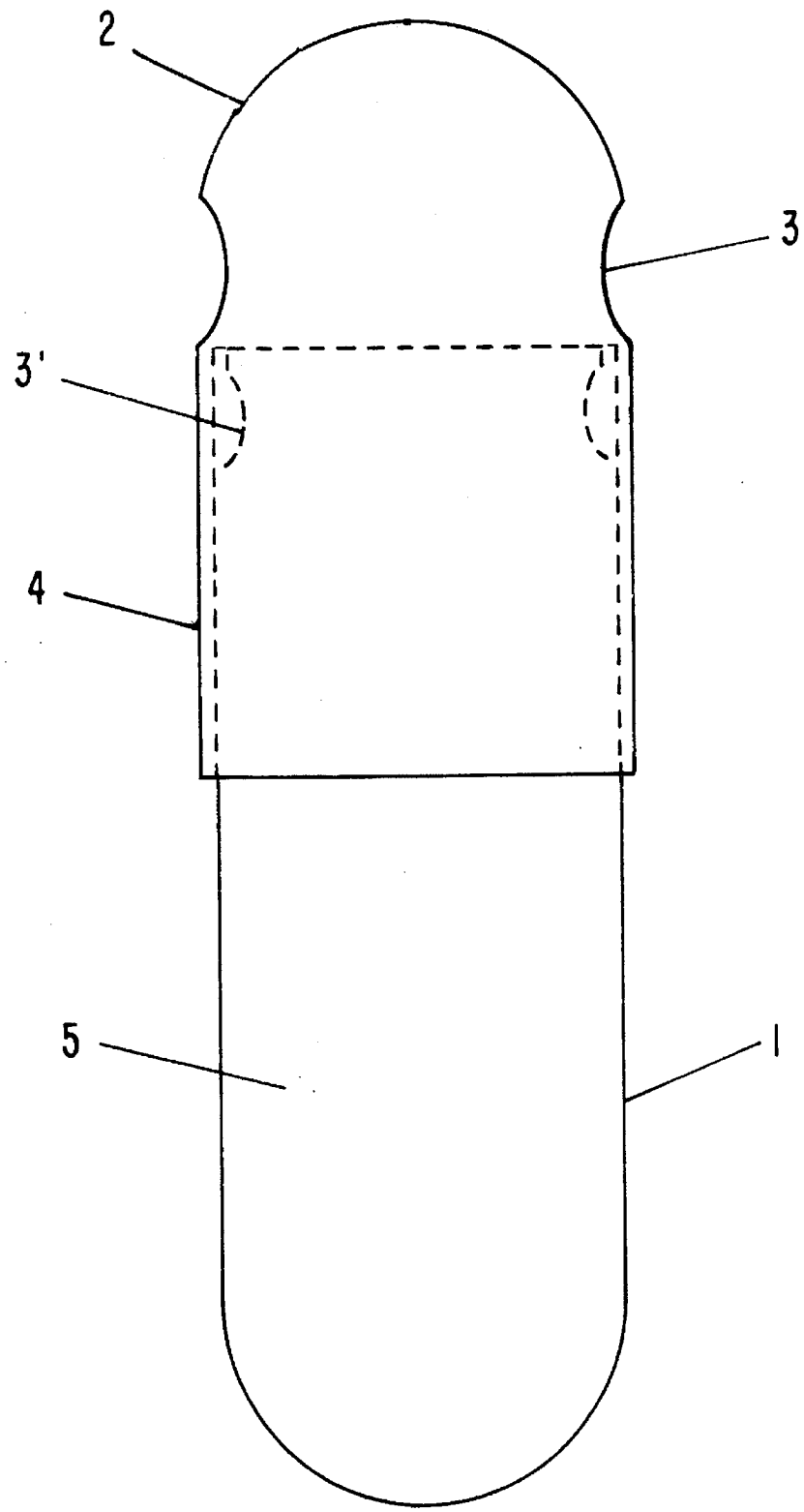
FIG. 1 shows schematically one embodiment of the capsule of the present invention.

As an example, there is used, in the medicament of this invention, a capsule which comprises a cup-shaped lower portion 1 connected to the cover 2 of the capsule by a flexible strip 4 that forms a hinge. The cup-shaped member 1 and the cover 2 (which has a shape matching that of the cup-shaped member) have, for example, in an area opposite the hinge, a small step 3, 3' forming a catch to close the capsule when the capsule has been filled with the medicament. It is then clear that it is easy, by a mere pressure on the cup shaped member to make the step escape from the lower edge of the cover, which cover is also generally in the shape of a small cup, in order to open the capsule and to easily empty it, without being able to close the capsule again.

In general, the capsule has a circular cross-section, the cup-shaped member 1 and the cover 2 being slightly bulged, but this shape can easily be substituted by any other suitable shape, such as a square shape enabling thus, as in the case of a round shape, an easy stacking in a box for packing the medicament.

Each capsule is generally filled with a magnesium salt medicament having the following composition, for one capsule:

| | |
|---|---|
| Magnesium sulphate 3H$_2$O | 355 mg |
| Saccharomyces yeast | 50 mg |
| Sodium saccharinate | 5 mg |
| Sodium cyclamate | 10 mg |
| Citric acid | 10 mg |
| Orange flavorings | 10 mg |
| Aerosil | 1 mg |

Obviously, with the same type of medicament, it is possible to use other therapeutically active components instead of the magnesium salt used as an active ingredient in the above mentioned example.

For testing the medicament, ten children to be treated by a magnesium salt medicament over a period of several weeks, were divided into two groups. Five children (first group) received a magnesium salt composition to which was added sacchoromyces yeast, sodium saccharinate, sodium cyclamate and a pharmaceutically acceptable excipient.

The first group of five children was treated with the medicament as described in the above mentioned example and in the form of the above described capsule.

The second group of five children used drinkable ampullas containing magnesium sulphate.

Secondary reactions were observed for the second group of five children, in particular stomach pains, and one child experienced diarrhoea which was difficult to cure.

For the first group of five children, no secondary reactions were observed. The medicament of the invention is apparently thus perfectly tolerated and, in any case, substantially better tolerated than that of the corresponding drinkable ampullas.

What is claimed is:

1. The combination of a medicament with a capsule, said combination having a pediatric presentation facilitating ingestion of the medicament by a child, the medicament being an anhydrous powder mixable with food so as to be easily ingested by a child, wherein said capsule contains a unit dose of the medicament and is formed by a small container comprising a cup-shaped bottom with a top portion, a cup-shaped cover having a shape matching the shape of said cup-shaped bottom, and a flexible strip for connecting said top portion to said cover, said capsule further comprising a catch for maintaining said cover on said cup-shaped bottom, said catch being comprised of a step at said cup-shaped bottom and a matching step at said cup-shaped cover catching said step of said cup-shaped bottom, wherein by pressing on said cup-shaped bottom said catch is released for opening said capsule, wherein said capsule once open cannot be closed again.

2. The combination of a medicament with a capsule, said combination having a pediatric presentation facilitating ingestion of the medicament by a child, the medicament being an anhydrous powder mixable with food so as to be easily ingested by a child, wherein said capsule contains a unit dose of the medicament and is formed by a small container comprising a cup-shaped bottom with a top portion, a cover having a shape matching the shape of said top portion of said cup-shaped bottom, and a means for removably connecting said cup-shaped bottom to said cover, said means being easily operated for opening said capsule, wherein said capsule once open cannot be closed again, and wherein the medicament is comprised of:

| | |
|---|---|
| magnesium sulphate × 3H$_2$O | 355 mg |
| saccharomyces yeast | 50 mg |
| sodium saccharinate | 5 mg |
| sodium cyclamate | 10 mg |
| citric acid | 10 mg |
| orange flavoring agent | 10 mg |
| Aerosil | 1 mg. |

3. The combination according to claim 1, wherein the medicament is comprised of:

| | |
|---|---|
| magnesium sulphate × 3H$_2$O | 355 mg |
| saccharomyces yeast | 50 mg |
| sodium saccharinate | 5 mg |
| sodium cyclamate | 10 mg |
| citric acid | 10 mg |
| orange flavoring agent | 10 mg |
| Aerosil | 1 mg |

4. The combination according to claim 1, wherein said unit dose comprises a therapeutically active ingredient as the main ingredient.

* * * * *